United States Patent
Hsieh et al.

(10) Patent No.: US 11,785,975 B2
(45) Date of Patent: Oct. 17, 2023

(54) METHOD FOR REDUCING BLOOD URIC ACID CONCENTRATION AND FOR DEGRADING PURINE

(71) Applicant: GLAC BIOTECH CO., LTD., Tainan (TW)

(72) Inventors: Pei-Shan Hsieh, Tainan (TW); Hsieh-Hsun Ho, Tainan (TW); Yi-Chun Tsai, Tainan (TW); Chung-Wei Kuo, Tainan (TW)

(73) Assignee: GLAC BIOTECH CO., LTD., Tainan (TW)

( * ) Notice: Subject to any disclaimer, the term of this patent is extended or adjusted under 35 U.S.C. 154(b) by 212 days.

(21) Appl. No.: 17/349,366

(22) Filed: Jun. 16, 2021

(65) Prior Publication Data

US 2022/0104527 A1    Apr. 7, 2022

Related U.S. Application Data

(62) Division of application No. 16/298,233, filed on Mar. 11, 2019, now abandoned.

(30) Foreign Application Priority Data

Jan. 3, 2019 (CN) .......................... 201910004073.0

(51) Int. Cl.
| | | |
|---|---|---|
| A23L 33/135 | (2016.01) | |
| A61K 35/747 | (2015.01) | |
| A61K 9/00 | (2006.01) | |
| A61P 13/00 | (2006.01) | |

(52) U.S. Cl.
CPC .......... *A23L 33/135* (2016.08); *A61K 9/0053* (2013.01); *A61K 35/747* (2013.01); *A61P 13/00* (2018.01); *A23V 2002/00* (2013.01); *A23V 2200/30* (2013.01); *A23Y 2220/35* (2013.01); *A23Y 2220/71* (2013.01)

(58) Field of Classification Search
None
See application file for complete search history.

(56) References Cited

U.S. PATENT DOCUMENTS

2004/0071680 A1    4/2004 Song et al.

FOREIGN PATENT DOCUMENTS

| CN | 1812801 A | 8/2006 |
| EP | 1649863 A | 4/2006 |
| EP | 2457576 A | 5/2012 |

OTHER PUBLICATIONS

Araya et al., Guidelines for the Evaluation of Probiotics in Food, Report of a Joint FAO/WHO Working Group on Drafting Guidelines for the Evaluation of Probiotics in Food, Apr. 30 and May 1, 2002, London Ontario, Canada, 11 pages.
Rudnick et al., "Oral Solid Dosage Forms", In Remington: The Science and Practice of Pharmacy, 21st Edition; 2005, Chapter 45; Lippincott Williams & Wilkins: Philadelphia, PA; pp. 889-928.

*Primary Examiner* — Michelle F. Paguio Frising
(74) *Attorney, Agent, or Firm* — Locke Lord LLP; Tim Tingkang Xia, Esq.

(57) ABSTRACT

A food composition and pharmaceutical composition with strains of lactic acid bacteria for reducing blood uric acid concentration are provided, comprising at least one or two isolated lactic acid bacteria strains selected from the following two: TSF331 (*Lactobacillus fermentum*) and TSR332 (*Lactobacillus reuteri*).

9 Claims, 5 Drawing Sheets

METHOD FOR REDUCING BLOOD URIC ACID CONCENTRATION AND FOR DEGRADING PURINE

CROSS-REFERENCE TO RELATED APPLICATIONS

This is a Divisional Application of U.S. patent application Ser. No. 16/298,233, filed Mar. 11, 2019. This Divisional application claims the benefit of the U.S. patent application Ser. No. 16/298,233.

BACKGROUND OF THE INVENTION

1. Field of the Invention

The present invention relates to a method for reducing blood uric acid concentration and for degrading purine, particularly to a method administering a food composition and pharmaceutical composition with strains of lactic acid bacteria for reducing blood uric acid concentration and for degrading purine.

2. Description of the Prior Art

As the dietary habit of people has been significantly changed by fast social development and prosperous economic growth, hyperuricemia is more and more popularized in China, Japan and Taiwan. The patients of hyperuricemia are likely to suffer from gout, which results from the inflammation induced by urate crystal and brings about serious aching in the joints of limbs. Hyperuricemia may also cause kidney diseases, urinary tract calculi, cardiovascular diseases, cerebrovascular diseases, etc. Further, hyperuricemia is also regarded as a risk factor for arteriosclerosis. Therefore, the medical field pays much attention to the prevention and treatment of hyperuricemia.

Hyperuricemia is a chronical disease, attributed to too high a concentration of blood uric acid. Uric acid is a final product of the metabolism of purine in human bodies. Purine is catabolized into uric acid by livers, and uric acid is excreted out of human bodies by kidneys. If the human body generates too much uric acid or the kidneys do not function well, the concentration of uric acid will be too high in blood.

In general, one third of purine is originated from food, and two thirds are generated by the metabolism of nucleic acid of cells. Therefore, hyperuricemia may result from the following factors: (1) ingesting too much food that is rich in purine or enhances the synthesis of purine; (2) increased synthetic metabolism of uric acid (endogenic uric acid overproduction); and (3) degradation of uric acid secretion function of kidneys.

Colchicine and non-steroidal anti-inflammatory drugs are usually used in treating gout. However, they are likely to disturb the functions of the stomach and intestines, the central nervous system, the liver, the kidneys, the hematopoiesis, etc. The uric acid production/synthesis inhibitors and the uric acid excretion promoters are usually used in treating hyperuricemia. However, the patients have to compromise the quality of life to take these drugs for a lifetime.

Therefore, it is urgent to develop a nutrition supplement (health food) able to persistently prevent from occurrence and recurrence of gout. Because one third of purine in human bodies comes from food, it is a very important strategy for hyperuricemia prevention to decrease the intake of purine.

In 2004, a Japan pharmaceutical company Otsuka proposed a patented combination composition containing lactic acid bacteria strains and yeast strains (CN 1812801A and EP1649863A1), which can lower the blood uric acid concentration. The patented strains include three strains of *Lactobacillus fermentum* ONRIC b0185, ONRIC b0193 and ONRIC b0195, and a strain of *Lactobacillus pentosus* ONRIC b0223. According to in-vitro purine degrading ability, Ogawa of Japan Kyoto University selected 13 strains (including *L. mali, L. vaccinostercus, L. brevis, L. fermentum, L. homohiochii, L. pentosus,* etc.) from 267 lactic acid bacteria strains (including *Bifidobacterium* hg, *Lactobacillus, Enterococcus, Leuconostoc, Pediococcus,* etc.). Then, the 3 patented lactic acid bacteria strains were selected in in-vivo experiments using mice suffering hyperuricemia. The experiments show that most of the strains cannot decrease serum uric acid except the abovementioned 3 strains.

So far, no international document has announced that the lactic acid bacterium *Lactobacillus reuteri* can reduce blood uric acid and prevent from gout except a patent (EP 2457576 A1) of a Poland company Eurochit Danuta Kruszewska. The patented strain of *Lactobacillus reuteri* DAN080 is applied to the patients of gout, wherein the combination including the bacteria bodies (dead or live), concentrated ferment liquid, and a secondary metabolite (ruterin) is used to enhance the activity of the immunological system of the host, whereby to treat or prevent from gout. However, the data published by the company only proves that *Lactobacillus reuteri* has the effect of relaxing discomfort of patients and the effect of anti-inflammation. The published data neither mention whether the strains can decompose purine nor mention whether eating the strains can decrease the blood uric acid concentration of the patients.

So far, only few strains have been experimentally confirmed to have the effect of decreasing blood uric acid concentration. The functionality of lactic acid bacteria to health is not based on the species of bacteria but dependent on the specificities of strains. The strains favorable to health are called the probiotics (Guidelines for the evaluation of probiotics in food; Report of joint FAO/WHO working group on drafting guidelines for the evaluation of probiotics in food; London Ontario, Canada Apr. 30 and May 1, 2002:1-7).

It is learned from the above introduction: the lactic acid bacteria, which are able to decompose purine, enhance immunity and inhibit inflammation, should have the potential to improve hyperuricemia and prevent from occurrence and recurrence of gout. Besides the bacteria strains used in patents, such as the strains of *L. oris, L. gasseri,* and *L. fermentum,* the Inventors also investigated the lactic acid bacteria having immunomodulatory functions and having the characteristics of probiotics. The Inventors screened these lactic acid bacteria strains according the ability of decomposing purine in vitro and then used animal experiments to evaluate the effect of decreasing blood uric acid to find out the strains having better effect of decreasing uric acid in blood.

SUMMARY OF THE INVENTION

The present invention provides a method administering a food composition and pharmaceutical composition with strains of lactic acid bacteria for reducing blood uric acid concentration, which can prevent from and/or treat hyperuricemia.

In one embodiment, the present invention provides a method for reducing blood uric acid concentration, comprising administering a food composition with strains of lactic acid bacteria to a subject, wherein the food composition comprises an isolated lactic acid bacteria strain and a physiologically-acceptable excipient or diluent. The lactic acid bacteria strain comprises at least one of a TSF331 strain of *Lactobacillus fermentum* (CGMCC No. 15527) and a TSR332 strain of *Lactobacillus reuteri* (CGMCC No. 15528).

In another embodiment, the present invention provides a method for reducing blood uric acid concentration, comprising administering a pharmaceutical composition with strains of lactic acid bacteria to a patient, wherein the pharmaceutical composition comprises an isolated lactic acid bacteria strain and a pharmaceutically-acceptable excipient or diluent. The lactic acid bacteria strain comprises at least one of a TSF331 strain of *Lactobacillus fermentum* (CGMCC No. 15527) and a TSR332 strain of *Lactobacillus reuteri* (CGMCC No. 15528).

In yet another embodiment, the present invention provides a method for degrading purine, comprising administering a composition with strains of lactic acid bacteria to a subject, wherein the composition comprises an isolated lactic acid bacteria strain and a physiologically-acceptable or pharmaceutically-acceptable excipient or diluent. The lactic acid bacteria strain comprises at least one of a TSF331 strain of *Lactobacillus fermentum* (CGMCC No. 15527) and a TSR332 strain of *Lactobacillus reuteri* (CGMCC No. 15528).

Below, embodiments are described in detail in cooperation with the attached drawings to make easily understood the objectives, technical contents, characteristics and accomplishments of the present invention.

DESCRIPTION OF THE PREFERRED EMBODIMENTS

Figure 1:
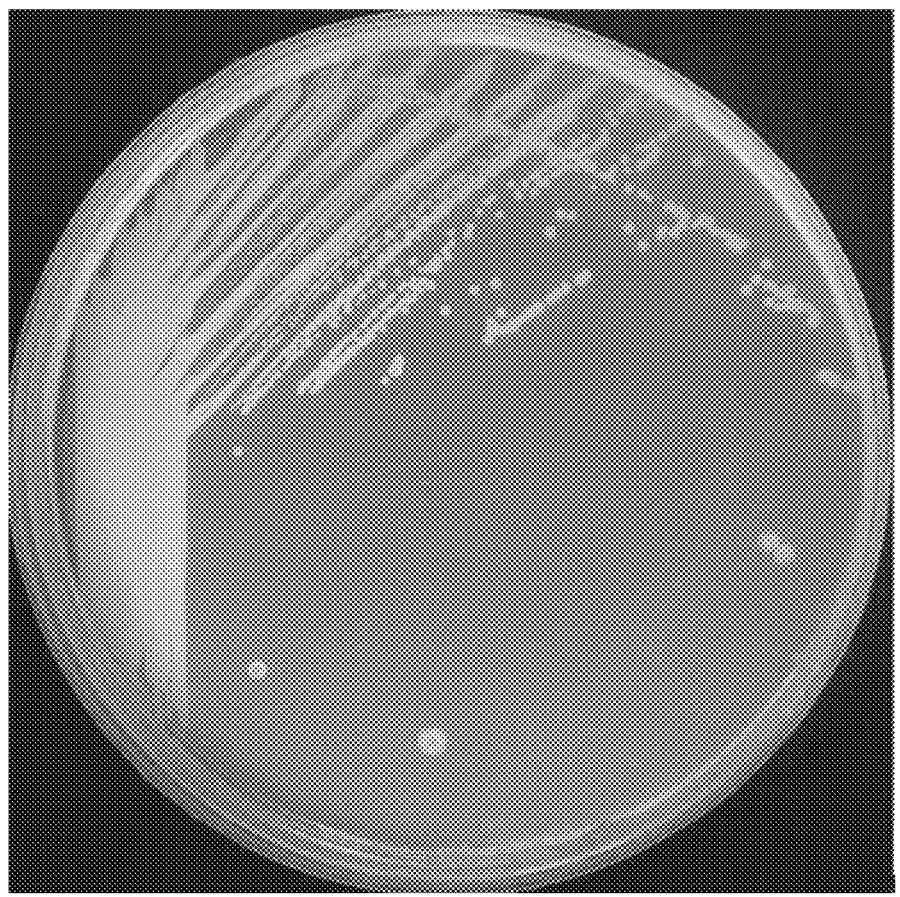
FIG. 1 shows the appearance of colonies of *Lactobacillus fermentum* according to one embodiment of the present invention.

The present invention will be described in detail with embodiments and attached drawings below. However, these embodiments are only to exemplify the present invention but not to limit the scope of the present invention. In addition to the embodiments described in the specification, the present invention also applies to other embodiments. Further, any modification, variation, or substitution, which can be easily made by the persons skilled in that art according to the embodiment of the present invention, is to be also included within the scope of the present invention, which is based on the claims stated below. Although many special details are provided herein to make the readers more fully understand the present invention, the present invention can still be practiced under a condition that these special details are partially or completely omitted. Besides, the elements or steps, which are well known by the persons skilled in the art, are not described herein lest the present invention be limited unnecessarily. Similar or identical elements are denoted with similar or identical symbols in the drawings. It should be noted: the drawings are only to depict the present invention schematically but not to show the real dimensions or quantities of the present invention. Besides, matterless details are not necessarily depicted in the drawings to achieve conciseness of the drawings.

The freeze-dried cultures of the strains of lactic acid bacteria mentioned in the specification are deposited in China General Microbiological Culture Collection Center (CGMCC) of Chinese Academy of Sciences (NO. 1 West Beichen Road, Chaoyang District, Beijing 100101, China). The details thereof are listed in Table. 1.

TABLE 1

Data of Deposited Strains of Lactic Acid Bacteria

| Strain | Specie | Deposition No. | Deposition Date |
|---|---|---|---|
| TSF331 | *Lactobacillus fermentum* | CGMCC No. 15527 | Mar. 29, 2018 |
| TSR332 | *Lactobacillus reuteri* | CGMCC No. 15528 | Mar. 29, 2018 |

The two lactic acid bacteria strains listed in Table. 1, which are respectively the TSF331 strain of *Lactobacillus fermentum* (CGMCC No. 15527) and the TSR332 strain of *Lactobacillus reuteri* (CGMCC No. 15528), are able to decompose purine and decrease blood uric acid concentration. Therefore, they can prevent from/treat hyperuricemia and prevent from occurrence of gout.

In one embodiment, the present invention provides a food composition with strains of lactic acid bacteria for reducing blood uric acid concentration, which comprises an isolated lactic acid bacteria strain and a physiologically-acceptable excipient or diluent. The lactic acid bacteria strain comprises at least one of a TSF331 strain of *Lactobacillus fermentum* (CGMCC No. 15527) and a TSR332 strain of *Lactobacillus reuteri* (CGMCC No. 15528). Each of the lactic acid bacteria strains is an active one. The term "active strain" means the lactic acid bacteria strains of the present invention can proliferate. The physiologically-acceptable excipient/diluent is a food. The food may be but is not limited to be dairy food, tea, coffee, or a combination thereof. The dairy food may be fermented milk, yoghurt, cheese, or powdered milk. The number of the lactic acid bacteria strains may be over $10^6$ CFU (Colony-Forming Unit), preferably $10^{10}$ CFU.

In another embodiment, the present invention provides a pharmaceutical composition with strains of lactic acid bacteria for reducing blood uric acid concentration, which comprises an isolated lactic acid bacteria strain and a pharmaceutically-acceptable excipient or diluent. The lactic acid bacteria strain comprises at least one of a TSF331 strain of *Lactobacillus fermentum* (CGMCC No. 15527) and a TSR332 strain of *Lactobacillus reuteri* (CGMCC No. 15528). Each of the lactic acid bacteria strains is an active one. The pharmaceutic composition may be in form of an oral dosage, such as a tablet, a capsule, a solution, or a powder. The number of the lactic acid bacteria strains may be over $10^6$ CFU (Colony-Forming Unit), preferably $10^{10}$ CFU.

In fact, it is learned from the experimental results mentioned below: the tested lactic acid bacteria strains are not necessarily able to decrease blood uric acid concentration. Since the Otsuka pharmaceutical company proposed its patent, there have been some other researches about the effect of lactic acid bacteria on decreasing blood uric acid concentration. There are also researches about different mechanisms of decreasing uric acid. For example, some researches undertook in-vitro experiments to screen the strains able to inhibit purine nucleoside phosphorylase or xanthine oxidase. However, the characteristics of these strains need to be further examined with experiments. The strains do not necessarily all have the same characteristics and the same experimental results.

It should be particularly mentioned: the present invention does not extensively claim all lactic acid bacteria strains but only claims the two strains deposited in China General Microbiological Culture Collection Center (CGMCC), which are respectively the TSF331 strain of *Lactobacillus fermentum* (CGMCC No. 15527) and the TSR332 strain of *Lactobacillus reuteri* (CGMCC No. 15528).

Below, the taxonomic characteristics of the strains are identified with the 16S rDNA sequencing analysis and the API bacterial identification system. The morphologies and general properties of the strains are listed in Table. 2.

TABLE 2

Figure 2:
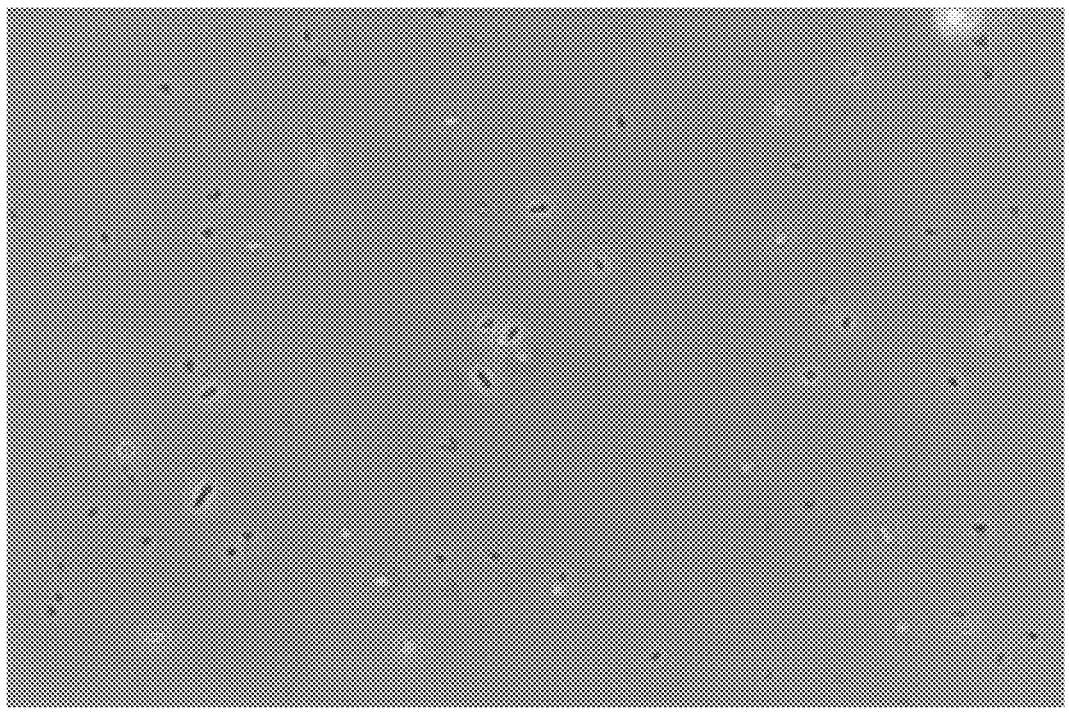
FIG. 2 shows the morphology of *Lactobacillus fermentum* according to one embodiment of the present invention.
Figure 3:
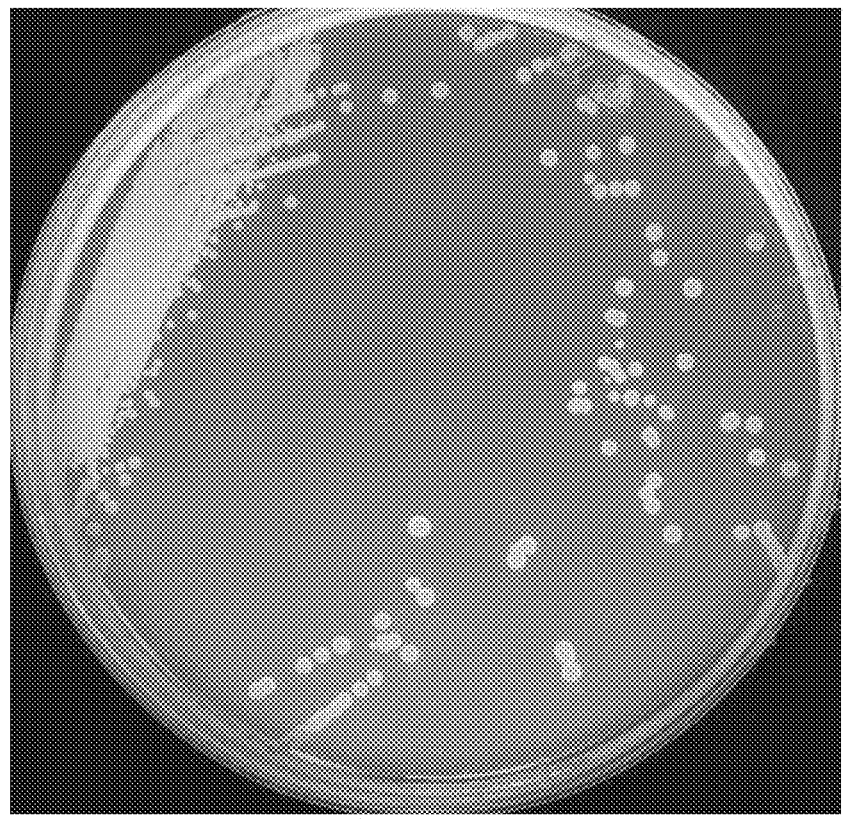
FIG. 3 shows the appearance of colonies of *Lactobacillus reuteri* according to one embodiment of the present invention.
Figure 4:
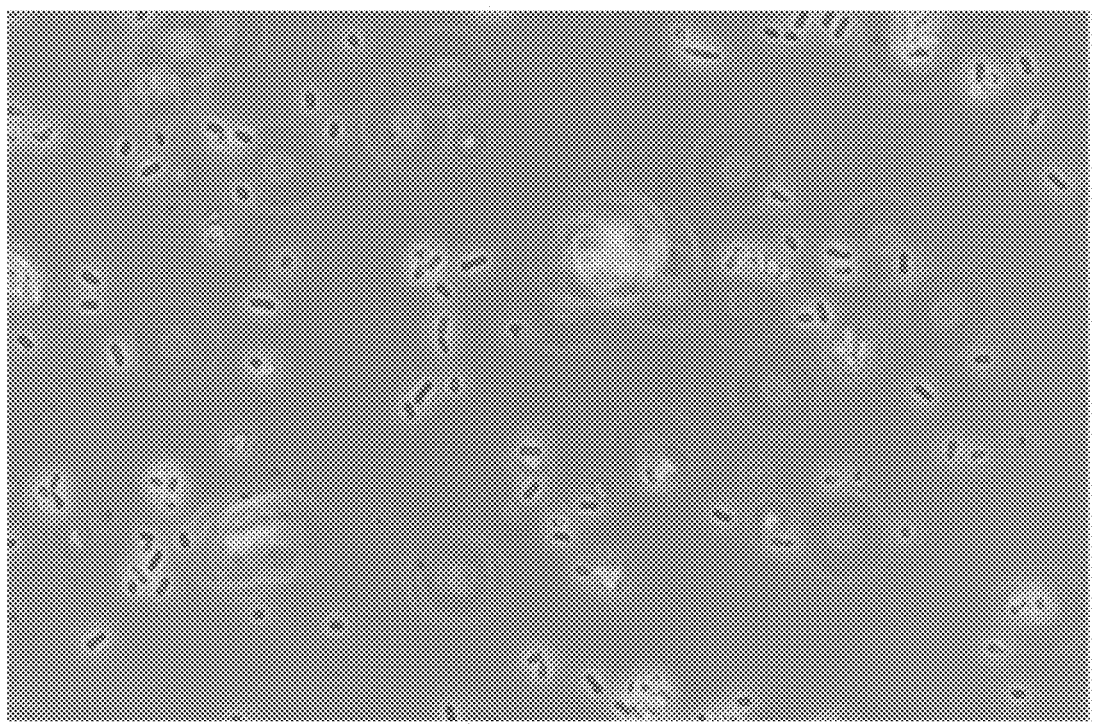
FIG. 4 shows the morphology of *Lactobacillus reuteri* according to one embodiment of the present invention.

| Strain | Morphology and Characteristics |
|---|---|
| TSF331 strain of *Lactobacillus fermentum* | 1. While TSF331 is cultured in the MRS agar medium, the colony thereof has a shape of a solid circle and a color of white (as shown in FIG. 1), the bodies of the bacteria each have a shape of a short rod, and the ends of the body are circular-shaped. They often appear in single bodies (as shown in FIG. 2).<br>2. They are gram-positive bacilli, unlikely to generate spores, free of catalase, oxidase and motility, able to grow in aerobic and anaerobic environments, most suitable to grow at a temperature of 37 ± 1° C. They belong to a facultative heterofermentative strains and do not generate gas in glucose metabolism. |
| TSR332 strain of *Lactobacillus reuteri* | 1. While TSR332 is cultured in the MRS agar medium, the colonies thereof each have a shape of a solid circle and a color of white (as shown in FIG. 3), the bodies of the bacteria each have a shape of a short rod, and the ends of the body are circular-shaped. They often appear in single bodies (as shown in FIG. 4).<br>2. They are gram-positive bacilli, unlikely to generate spores, free of catalase, oxidase and motility, able to grow in aerobic and anaerobic environments, most suitable to grow at a temperature of 37 ± 1° C. They belong to a facultative heterofermentative strains and do not generate gas in glucose metabolism. |

Next, experiments are used to evaluate the purine decomposition ability of the lactic acid bacteria strains claimed by the present invention. In one embodiment of the present invention, in-vitro purine decomposition experiments of five kinds of lactic acid bacteria strains (listed in Table. 3) are undertaken.

TABLE 3

| | |
|---|---|
| Example 1 | TSF331 (of *Lactobacillus fermentum*) claimed by the present invention |
| Example 2 | TSR332 (of *Lactobacillus reuteri*) claimed by the present invention |
| Comparison 1 | *Lactobacillus brevis* (BCRC 14045) |
| Comparison 2 | *L. gasseri* (BCRC 17616) |
| Comparison 3 | *L. plantarum* (Lp323) |
| Comparison 4 | *L. acidophilus* (La322) |

*Lactobacillus brevis* and *L. gasseri* are purchased from Bioresource Collection and Research Center. *L. plantarum* is purchased from American Type Culture Collection.

The abovementioned lactic acid bacteria strains are preserved in a solution containing 20% glycerol at a temperature of −80° C. Before experiments, the strains are activated two times at a temperature of 37° C. for 24 hours with an MRS broth (DIFCO) containing 0.05% cysteine. The in-vitro purine decomposition experiment includes the following steps:

1. Activate the lactic acid bacteria strains, which are preserved in glycerol at a temperature of −80° C., with the MRS broth (DIFCO); inoculate 2% (v/v) of each lactic acid bacteria strain to a fresh MRS broth; anaerobically culture the MRS brothes containing lactic acid bacteria strains at a temperature of 37° C. overnight; centrifugalize the cultured MRS brothes at a speed of 3000 rpm for 10 minutes (at a temperature of 4° C.) to collect the bacteria bodies.

2. Use the bacteria bodies and a 0.1M phosphate buffer solution to prepare suspension liquids containing bacteria at a concentration of $1\times10^9$ CFU/ml.

3. Add two types of purines, which are respectively inosine and guanosine (purchased from Sigma), to the abovementioned suspension liquids to make the final concentrations of them be 1.26 mM; place the suspension liquids in an incubator rotating at a horizontal rotation speed of 140 rpm at a temperature of 37° C. for 30 minutes to 2 hours for reaction.

4. Use 0.1M HClO4 to terminate the reactions; suck 200 μl of product liquid from each group; centrifugalize the bottom bacteria bodies; use a 0.22 μm filter membrane to filter the supernatant liquids; take 50 μl of filtered liquid for high performance liquid chromatography (HPLC) analysis with analysis conditions: column: RP-18(MERCK); radius: 5 μm; size: 4.6×250 mm; flowrate: 1 ml/min; mobile phase: A: 0.1% acetic acid, B: methanol; gradient A/B (min): 2% (0 min), 20% (10 min), 20% (13 min), 2% (15 min).

5. Use a photodiode array (HITACHI L-2455) to detect a light with a wavelength of 254 nm.

The formula for calculating the purine residual rate is expressed as

Purine residual rate (%)=[(1−$A$ (mM))/1.26 (mM)]× 100% wherein A=the post-reaction purine concentration.

The experimental results of the abilities of the abovementioned lactic acid bacteria strains in decomposing inosine and guanosine are shown in Table. 4.

TABLE 4

| | Purine residual rate (%) | | | |
|---|---|---|---|---|
| | inosine | | guanosine | |
| | 0 hour reaction | 1 hour reaction | 0 hour reaction | 1 hour reaction |
| Control group | 100 | 100 | 100 | 100 |
| Example 1 | 100 | 44 | 100 | 15 |
| Example 2 | 100 | 0 | 100 | 0 |
| Comparison 1 | 100 | 50 | 100 | 15 |
| Comparison 2 | 100 | 51 | 100 | 13 |
| Comparison 3 | 100 | 32 | 100 | 44 |
| Comparison 4 | 100 | 38 | 100 | 12 |

The experimental results show that Example 1, Example 2, Comparison 3 and Comparison 4 have better ability in degrading inosine and guanosine. Especially, the concentrations of inosine and guanosine are both reduced from 100% to 0% within one hour in Example 2. The purine degrading speed of Example 2 is 2 times that of the other groups.

Therefore, Example 2 obviously has better purine degrading ability. The experimental results show that the lactic acid bacteria strains claimed by the present invention have better purine degrading ability than that of a portion of Comparisons.

HPLC is used to analyze the metabolite produced in a one-hour purine degradation of each group, and the results are shown in Table. 5.

TABLE 5

| | Metabolite of purine degradation (%) | | |
|---|---|---|---|
| | Hypoxanthine | Guanine | Uric acid |
| Example 1 | 76 | 83 | 0 |
| Example 2 | 86 | 77 | 0 |
| Comparison 1 | 73 | 61 | 0 |
| Comparison 3 | 95 | 73 | 0 |
| Comparison 4 | 82 | 70 | 0 |

Different groups of lactic acid bacteria strains respectively have different concentrations of the metabolites of purine degradations. The metabolites of purine degradation are mainly guanine and hypoxanthine, and no uric acid exists therein.

According to the abovementioned experimental results, the strains able to degrade purine are selected to feed rats suffering hyperuricemia to verify the ability of these strains in decreasing blood uric acid. The Inventors referred to the method established by Li, et al. (PLoS One. 2014 Sep. 3; 9(9):e105577. doi: 10.1371/journal.pone.0105577) for the experiment of verifying the ability of decreasing blood uric acid. The experiment of verifying the ability of decreasing blood uric acid includes the following steps:

1. Provide SPF-grade 30-day-old male Wistar rats; feed the rats with AIN-93G forage and sterile water for a week; collect blood from the eye sockets in a non-fast state; set the blood still for 30 minutes at an ambient temperature, and centrifugalize the blood at a speed of 3500 rpm for 10 minutes to obtain serum; store the serum at a temperature of −80° C. to make ready for detecting uric acid concentration.

2. Divide the rats into the groups listed in Table. 6,

TABLE 6

| Group | | Forage | Tube-feeding lactic acid bacteria liquid 1 ml/day ($10^9$ CFU/ml in 0.85% NaCl) | Abdomen-injecting Oxonate (0.35 mg/ 100 g BW) |
|---|---|---|---|---|
| Blank experiment group | | AIN-93G forage | — | — |
| Induced group | Comparison group | High purine forage | — | + |
| | Example 1 | High purine forage | TSF331 strain of Lactobacillus fermentum | + |
| | Example 2 | High purine forage | TSR332 strain of Lactobacillus reuteri | + |
| | Comparison 5 | High purine forage | L. plantarum (Lp323) + L. acidophilus (La322) | + | wherein each 100 g the high purine forage contain 87 g Yeast Extract (Sigma) and 1.5 g RNA (Torula Yeast) (R6625 Sigma). In this embodiment, Comparison 5 is a combination of Comparison 4 (*L. plantarum* (Lp323)) and Comparison 3 (*L. acidophilus* (La322)).

3. Raise the rats for 7 days; collect 1 ml of blood from the eye sockets in the eighth day; set the blood still for 30 minutes at an ambient temperature, and centrifugalize the blood at a speed of 3500 rpm for 10 minutes to obtain serum; store the serum at a temperature of −80° C. to make ready for detecting uric acid concentration.

Figure 5:
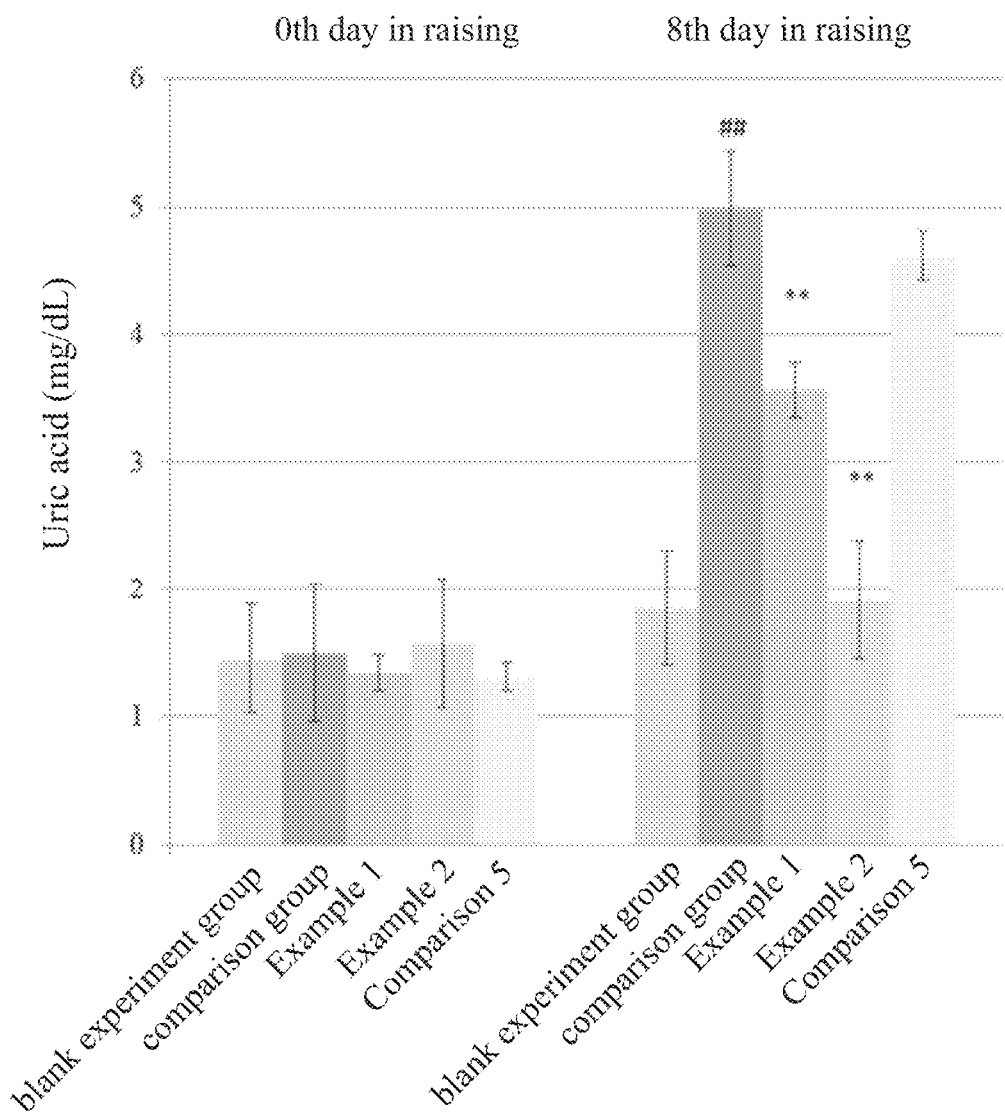
FIG. 5 shows the results of experiments using lactic acid bacteria strains to reduce blood uric acid according to one embodiment of the present invention.

The experimental results are shown in FIG. 5. In comparison with the blank experiment group, the comparison group, which no lactic acid bacteria strain is suppled to, has greatly increased blood uric acid concentration while they have been raised to the eighth day. In the groups, which the lactic acid bacteria strains are supplied to, the blood uric acid concentrations of Example 1 where the rats are fed with the TSF331 strain (of *Lactobacillus fermentum*) claimed by the present invention and Example 2 where the rats are fed with the TSR332 strain (of *Lactobacillus reuteri*) claimed by the present invention are significantly decreased, in comparison with that of the comparison group. The blood uric acid concentration of Comparison 5, which *L. plantarum* (Lp323) and *L. acidophilus* (La322) are simultaneously supplied to, does not change obviously while they have been raised to the eighth day, in comparison with that of the comparison group. In other words, the effect of *L. plantarum* (Lp323)+*L. acidophilus* (La322) is insignificant in decreasing blood uric acid concentration.

As shown in Table. 4, it is a special phenomenon: although *L. plantarum* (Lp323) in Comparison 3 and *L. acidophilus* (La322) in Comparison 4 are both able to degrade purine, the effect of *L. plantarum* (Lp323)+*L. acidophilus* (La322) in Comparison 5 is insignificant in decreasing blood uric acid concentration. Therefore, the lactic acid bacteria strains able to degrade purine are not necessarily able to decrease blood uric acid concentration. The TSF331 strain (of *Lactobacillus fermentum*) and the TSR332 strain (of *Lactobacillus reuteri*), which are claimed by the present invention, can exactly degrade purine and decrease blood uric acid concentration simultaneously.

In conclusion, the food composition and pharmaceutical composition with strains of lactic acid bacteria of the present invention can effectively degrade purine, generating neither degradation metabolites nor uric acid, and decreasing blood uric acid concentration significantly. Therefore, the present invention can apply to prevent from or treat hyperuricemia. In comparison with the conventional uric acid synthesis inhibitors and the conventional uric acid excretion promoters (such as Allopurino and Benzbromarone), the food composition and pharmaceutical composition with strains of lactic acid bacteria of the present invention generates less side effects and decreases blood uric acid more significantly, having high potential in controlling blood uric acid concentration and preventing from gout.

Bioresource Deposition

CGMCC No. 15527, Institute of Microbiology, Chinese Academy of Sciences, Mar. 29, 2018

CGMCC No. 15528, Institute of Microbiology, Chinese Academy of Sciences, Mar. 29, 2018

What is claimed is:

1. A method for reducing blood uric acid concentration, comprising administering a food composition to a subject in need thereof, wherein the food composition comprises: an isolated lactic acid bacterial strain, wherein the lactic acid bacterial strain comprises a TSR332 strain of *Lactobacillus reuteri*, and the TSR332 strain of *Lactobacillus reuteri* is deposited in China General Microbiological Culture Collection Center (CGMCC) of Chinese Academy of Sciences with CGMCC No. 15528; and a physiologically-acceptable excipient or diluent.

2. The method according to claim 1, wherein the lactic acid bacterial strain is a bacterial strain able to proliferate.

3. The method according to claim 1, wherein the excipient or diluent is a food.

4. The method according to claim 3, wherein the food is fermented milk, yoghurt, cheese, dairy food, powdered milk, tea, coffee, or a combination thereof.

5. A method for reducing blood uric acid concentration, comprising administering a pharmaceutical composition to a patient in need thereof, wherein the pharmaceutical composition comprises: an isolated lactic acid bacterial strain, wherein the lactic acid bacterial strain comprises a TSR332 strain of *Lactobacillus reuteri*, and the TSR332 strain of *Lactobacillus reuteri* is deposited in China General Microbiological Culture Collection Center (CGMCC) of Chinese Academy of Sciences with CGMCC No. 15528; and a pharmaceutically-acceptable excipient or diluent.

6. The method according to claim 5, wherein the lactic acid bacterial strain is a bacterial strain able to proliferate.

7. The method according to claim 5, which the pharmaceutical composition is in form of an oral dosage.

8. A method for degrading purine, comprising administering a composition to a subject in need thereof, wherein the composition comprises: an isolated lactic acid bacterial strain, wherein the lactic acid bacterial strain comprises a TSR332 strain of *Lactobacillus reuteri*, and the TSR332 strain of *Lactobacillus reuteri* is deposited in China General Microbiological Culture Collection Center (CGMCC) of Chinese Academy of Sciences with CGMCC No. 15528; and a physiologically-acceptable or pharmaceutically-acceptable excipient or diluent.

9. The method according to claim 8, wherein the lactic acid bacterial strain is a bacterial strain able to proliferate.

* * * * *